United States Patent [19]

Geiss et al.

[11] Patent Number: 5,287,758
[45] Date of Patent: Feb. 22, 1994

[54] TEMPERATURE CONTROLLED PIPETTE TUBE

[75] Inventors: Manfred Geiss, Frankfurt am Main; Wolfgang Heide, Darmstadt; Jurgen Wittekind, Frankfurt am Main; Michael Breetz, Steinberg, all of Fed. Rep. of Germany

[73] Assignee: Behringwerke AG, Marburg, Fed. Rep. of Germany

[21] Appl. No.: 57,517

[22] Filed: May 6, 1993

Related U.S. Application Data

[63] Continuation of Ser. No. 825,079, Jan. 24, 1992, abandoned.

[30] Foreign Application Priority Data

Jan. 26, 1991 [DE] Fed. Rep. of Germany ....... 4102336
Nov. 14, 1991 [EPX] European Pat. Off. ......... 91119406

[51] Int. Cl.$^5$ .................. B01L 03/02; H05B 03/14; H05B 01/02; H05B 06/10
[52] U.S. Cl. ................ 73/864.01; 73/863.11
[58] Field of Search ........... 73/864.01, 863.11, 863.01

[56] References Cited

U.S. PATENT DOCUMENTS 3,085,435  4/1963  Miscoe et al. ............... 73/863.11
3,664,178  5/1972  Spergel et al. ............... 73/863.11
3,872,718  3/1975  Nelson et al. ............... 73/863.11
4,312,835  1/1982  Zoltan et al. ............... 73/863.11
4,357,836  11/1982  Kokesh ..................... 73/863.11
4,670,219  6/1987  Nelson et al. ............... 73/863.11

FOREIGN PATENT DOCUMENTS 0192957  9/1986  European Pat. Off. .
2626332  2/1977  Fed. Rep. of Germany .
3838626  5/1990  Fed. Rep. of Germany .

OTHER PUBLICATIONS

American Hertiage Dictionary, New College Ed., p. 943, (Houghton Mifflin, 1982).

Primary Examiner—Hezron E. Williams
Assistant Examiner—George Dombroske
Attorney, Agent, or Firm—Finnegan, Henderson, Farabow, Garrett & Dunner

[57] ABSTRACT

A heatable pipette apparatus, includes a pipette tube having a first zone and second zone. The first zone includes a tip end and a first heater for heating the first zone. The second zone includes a second heater for heating the second zone. Regulators are provided for separately regulating the temperature of the first heater and the second heater, the first heater being able to more accurately and precisely alter the temperature of fluids in the tube to reach a predetermined temperature.

10 Claims, 1 Drawing Sheet

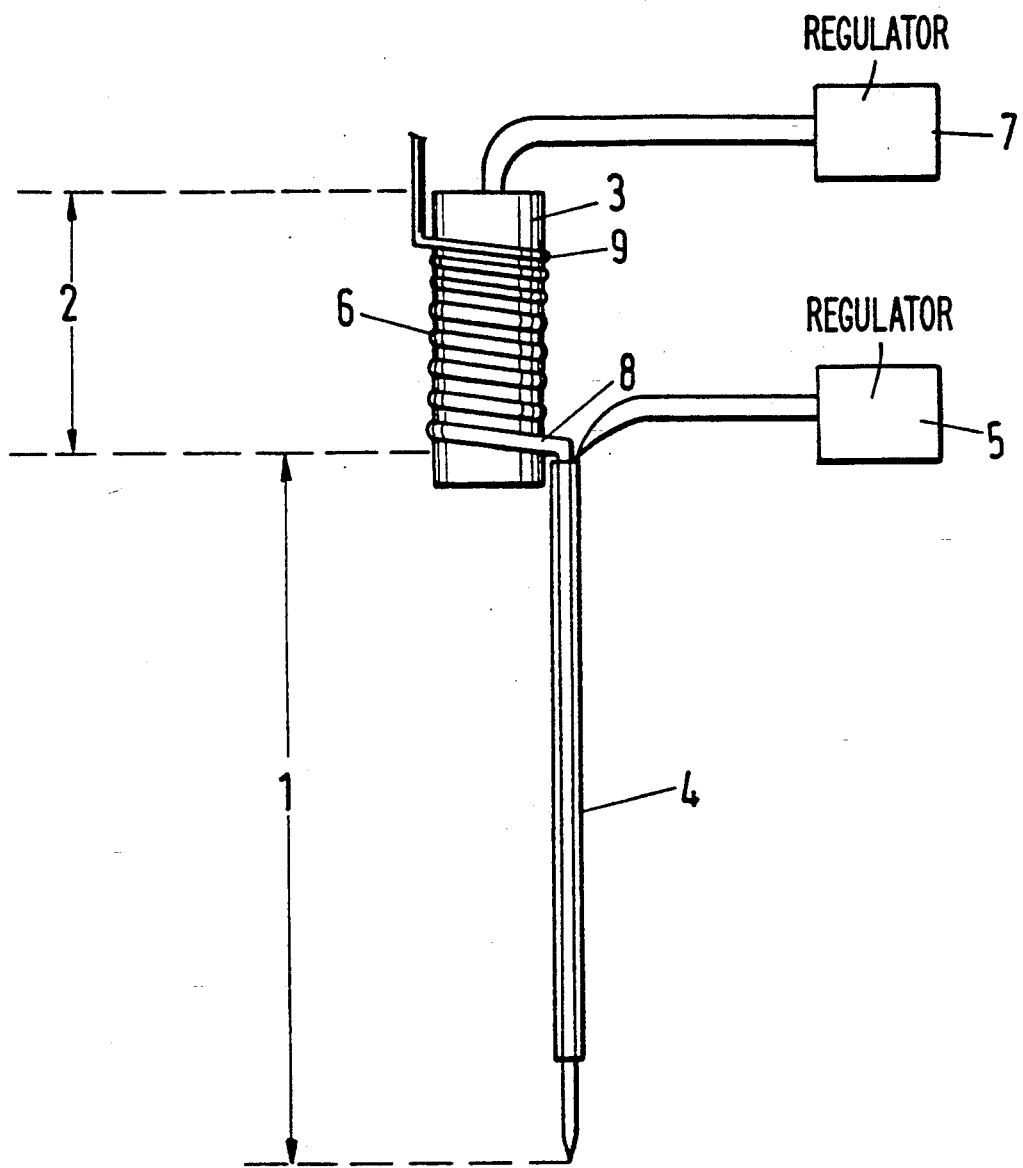

TEMPERATURE CONTROLLED PIPETTE TUBE

This application is a continuation, division, of application Ser. No. 07/825,079 filed Jan. 24, 1992, now abandoned.

BACKGROUND OF THE INVENTION

1. Field of the Invention

The invention relates to a heatable pipette tube with a controlled electric heater.

2. Descrition of the Related Art

A heatable pipette tube, such as the one described in Germ patent specification 26 26 332, permits regulatable heating extending over the pipette tube, with the exception of the tip end. A drawback of this design is that temperature control of samples is difficult. For example, if the heating and the regulation (control) is adjusted in order to temper larger volumes, there i a danger that smaller volumes may become overheted. Likewise, if the pipette is adjusted for small volumes, large samples may not become heated enough. There also exists a controllable heater for a centrifuge, into which a pipette tube may be inserted. However, temperature control with this arrangement is also problematic. That is, it is difficult to temper different volumes of pipette fluid quickly to a desired temperature without overheating the fluid.

EP-0 192 957 B1 describes an analysis device with a slide which transports via a pipette, fluid samples from a rotating plate to a tempered cuvette. The slide is provided with a controllable heater. This temperature controller pretempers the sample fluid to the temperature of the cuvette.

German Offenlegungsschrift 38 38 626 discloses a pipette tub hat is heated by electrically heated water. However, this heater lacks sufficient responsiveness because the water supply together with other structural parts must first be heated by the water to the desired temperature.

SUMMARY OF THE INVENTION

The present invention avoids the disadvantages of the related art. An object of the present invention is to provide a heatabl pipette tube in which different volumes can be brought very quickly to the correct dsired temperature.

This object is attained by providing the pipette tube with two zones, namely a first zone containing the tip of the pipette tube and comprising a relatively small pipette volume, and a second zone with a comparatively larger pipette volume. Both zones are provided with separate heaters each with its own regulator. The regulator provided for heating of the first zone works with greater corrective action of manipulated value while the regulator of the second zone works with smaller corrective action of manipulated value. In other words, the temperature of the contents in the first zone may be changed more quickly and accurately than the temperature of the liquid in the second zone, which is slower to move and has a larger area of heat transmission.

If a small volume is pipetted, it is quickly heated to the desired temperature. If a larger volume is pipetted, the pipette fluid is sucked into the second zone above the first zone, wherein the first zone acts as pretempering for the second zone. However, these volumes arrive in the second zone at temperatures that depend on pretempering that occurs in the first zone. Generally, there will be a relatively low temperature differences of some degrees between the zones.

Due to the different structure of the two zoes, temperature regulation of the second zone is more sluggish and is distinguished by small temperature fluctuations and by a larger area of heat transmission, in order to be able to temper larger volumes in a short period of time.

It is preferable for the tube of the first zone to be relatively straight and for the tube of the second zone to be twisted or wound, for example, in either a spiral or in a meander configuration. This structure facilitates the smaller heat capacity of the first zone and the larger heat capacity of the second zone.

It is also beneficial if the tube in the area of the second zone abutts a heat conductor, such as a metal block having an aperture for receiving the tube.

According to a preferred embodiment of the invention, the electrical heater of the first zone is a PTC (positive temperature coefficient) heater wherein the heating wire has a varying resistance. Thus, if the tube in the first zone is only partly filled with the pipette fluid, the PTC resistance wire in the unfilled part is heated more than part that does not contact the fluid. Due to this feature, a very even tempering may be obtained independent of the filling condition of the tube in the first zone.

A temperature sensor is provided at the entrance of the second zone so that the first temperature at the sde of the entrance is measured.

Additionally, a similar temperature sensor also can be provided at the egress of the second zone, which is beneficial for example for cleaning purposes, when the tube is filled in the reverse direction. For this reason, throughout the present application the zones are not referred to as lower and upper pipetting zones, but rather are referred to as a first and a second pipetting zone. Generally, the pipetting fluid is sucked through the tip to the first, lower zone, and then arrives in the second, upper zone, if a sufficient volume is present In a preferred embodiment, in the second zone, the temperature sensor, and the heating element are identical The pipette tube according to the invention may also be used for cooling. For this, the invention may include Peltier elements instead of the heating elements described above. Peltier elements, which are known, are used for both cooling or heating In a further preferred embodiment, the nominal temperature in the second zone is somewhat lower, preferably between 0,5 and 5° K. lower than in the first zone.

BRIEF DESCRIPTION OF THE DRAWING

The accompanying drawing, which is incorporated in and constitutes a part of this specification, illustrates one embodiment of the invention, and together with the description, seeks to explain the principles of the invention.

FIG. 1 is a schematic diagram of a preferred embodiment of the present invention.

DETAILED DESCRIPTION OF THE PREER EMBODIMENT

A preferred embodiment of the invention will now be described with further detail. FIG. 1 schematically illustrates a pipette tube according to the invention. The pipette tube includes a lower area 1 and a subsequent upper area 2. The lower area includes a pipette tip, and is characterized by a substantially linearly extending tube portion.

In the upper area 2, the tube may be spirally wound or may be wound in other manners such as meander configurations. The tube of upper area 2 abuts a body 3, constructed of material with goo heat conducting properties.

At least the largest length of the lower area 1 is heated by means of a first electrical heater 4 to which a regulator 5 is connected. Similarly, the upper area 2 of the tube is also heated by means of a second electrical heater 6, to which a regulator 7 is connected.

Thus, the total length 1, 2 of the tube is heated by two separated heaters 4, 6 wherein two different regulators 5, 7 with different regulating characteristics are utilized. The regulator 5 works with a strong corrective action of manipulated vale, ad the regulator 7 has a smaller corrective action of manipulated value. In other words, the first heater has a superior ability than the second heater to quickly and accurately alter the temperature of the fluid in the tube to reach a predetermined temperature. There is a difference in the range of adjustments between the heaters due to differences in the temperature changing magnitude of the regulatrs.

The first heater 4 heats the straight part of the tube up to, for example 15 mm before the tip. The second heater 6 includes an aluminum cylinder (body 3) with a large heat capacity. The greatest part of the tube in respect to its length is wound around the cylinder.

The regulating circuit 5 of the lower heater 4 regulates, without delay, the temperature of the quantity of fluid in the lower area 1. his means that great fluctuations in the nominal size are regulated very quickly. If cold fluid is received, it is heated near the desired temperature when passing the lower part o the tube (area 1). If it is received in the upper part 2 of the tube which is tempered by the upper heater 6, the temperature is adapted quickly and without great fluctuations because of the smaller heat capacity of the fluid compared to the aluminum cylinder 3 and because of the small difference in temperature of the fluid to the temperature of the cylinder. Thus, a regulating circuit with very small corrective action of manipulated value is used.

The advantage of the described regulation is a very small fluctuation (change) of the temperature at the nominal value. The disadvantage of the longer regulation time for strong flucuation of the nominal value thereby is not effective.

Tests have shown that with the pipette tube according to the invention, pipette fluids of, for example, 20 μm up to 600 μl can be pipetted wherein the different areas 1, 2 of the tube were utilized. In this case, the pipette fluid was heated within a few seconds to 37,3+/−0,3° C. The wall temperature of the tube should not exceed a temperature of 41° C. in order to avoid damage to the pipette fluid.

FIG. 1 also shows a temperature sensor 8 at the inlet of the second zone at the outlet of zone 2. A further temprature sensor 9 may also be provided at the outlet of zone 2. The temperature sensors 8, 9 are part of the regulating circuit of regulator 7.

In a preferred embodiment of the invention, the lower area 1 has a volume of 100 μl and the uappar area 2 a volume of 500 μl. However, volumetric relationships other than a 1:5 ratio of the volume of the lower area to the upper area are possible.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A heatable pipette apparatus for heating and maintaining a liquid conveyed in the pipette apparatus to a desired temperature, the pipette apparatus comprising:
   a pipette tube having a first zone and a second zone, the first zone including a tip end;
   first heating means for heating the first zone;
   second heating means for heating the second zone;
   first and second regulating means for separately regulating the temperature of the first heating means and the second heating means, respectively, the first regulating means rapidly adjusting the temperature of the liquid toward the desired temperature, and the second regulating means finely adjusting the temperature to achieve and maintain the desired temperature.

2. The apparatus according to claim 1 wherein the tip end includes an outlet of the pipette tube, and wherein a volume of liquid capable of being held in the second zone is greater than a volume of liquid capable of being held in the first zone.

3. The apparatus according to claim 1 wherien the tip end includes an outlet of the pipette tube, and wherein the first zone of the tube has a substantially linear shape and the second zone of the tube has a twisted shape.

4. The apparatus according to claim 1 wherein the second heating means includes a heat conducting material abutting the second zone.

5. The apparatus according to claim 1 wherein the first heating means includes a PTC-heater.

6. The apparatus according to claim 1 wherein at least one of said first and second regulating means includes a temperature sensor located between the first and second zones of the tube.

7. The apparatus according to claim 1 wherein at least one of said first and second regulating means further includes a temperature sensor located at an end of the second zone opposite the first zone.

8. The apparatus according to claim 1 wherein the first and second regulating means include respective first and second regulators, said first and second regulators being connected to the first and second heating means, respectively.

9. The apparatus according to claim 1 wherein the first and second heating means include Peltier elements.

10. A heatable pipette apparatus for heating and maintaining a liquid conveyed in the pipette apparatus to a desired temperature, the pipette apparatus comprising:
   a pipette tube having a first zone and a second zone, the first zone including a tip end;
   first heating means for heating the first zone;
   second heating means for heating the second zone;
   first regulating means for controlling the first heating means; and
   second regulating means for controlling the second heating means, the first and second regulating means being operable independently of each other.

* * * * *